(12) United States Patent
Ikarashi et al.

(10) Patent No.: US 8,609,352 B2
(45) Date of Patent: Dec. 17, 2013

(54) BIOASSAY METHOD FOR YOKUKANSAN WITH SEROTONIN RECEPTOR

(75) Inventors: Yasushi Ikarashi, Ibaraki (JP); Kyoji Sekiguchi, Ibaraki (JP); Kiyoshi Terawaki, Ibaraki (JP); Takuji Yamaguchi, Ibaraki (JP)

(73) Assignee: Tsumura & Co., Tokyo (JP)

( * ) Notice: Subject to any disclaimer, the term of this patent is extended or adjusted under 35 U.S.C. 154(b) by 48 days.

(21) Appl. No.: 12/867,514

(22) PCT Filed: Feb. 15, 2008

(86) PCT No.: PCT/JP2008/052550
§ 371 (c)(1),
(2), (4) Date: Aug. 13, 2010

(87) PCT Pub. No.: WO2009/101700
PCT Pub. Date: Aug. 20, 2009

(65) Prior Publication Data
US 2010/0317028 A1     Dec. 16, 2010

(51) Int. Cl.
*G01N 33/53* (2006.01)

(52) U.S. Cl.
USPC .......................................................... 435/7.2

(58) Field of Classification Search
None
See application file for complete search history.

(56) References Cited

U.S. PATENT DOCUMENTS

| 2004/0157917 | A1 | 8/2004 | Gobaille et al. |
| 2009/0098228 | A1 | 4/2009 | Ikarashi et al. |
| 2010/0196944 | A1 | 8/2010 | Ikarashi et al. |

FOREIGN PATENT DOCUMENTS

| JP | 2000 512621 | 9/2000 |
| JP | 2001 521876 | 11/2001 |
| JP | 2004 533843 | 11/2004 |
| JP | 2005 520486 | 7/2005 |
| JP | 2007 535480 | 12/2007 |

OTHER PUBLICATIONS

Kanatani et al. (1985) J. Pharm. Pharmacol. 37: 401-404.*
U.S. Appl. No. 13/000,029, filed Dec. 20, 2010, Ikarashi, et al.
Wook, Ji Jung et al., "Anxiolytic effects of the aqueous extract of *Uncaria rhynchophylla*", Journal of Ethnopharmacology, vol. 108, No. 2, pp. 193-197, (Nov. 24, 2006).
Komatsu, Yasuhiro et al., "Chotosan no Gakushu Shogai Kaizen Sayo (Ministry of Health and Welfare S)", Choju Kagaku Sogo Kenkyu, vol. 199, No. 9, pp. 101 to 105, (1998).
Newman-Tancredi, Adrian et al., "High-level stable expression of recombinant 5-HT 5-hydroxytryptamine receptors in Chinese hamster ovary cells", Biochem., J., vol. 285, pp. 933-938, (1992).
U.S. Appl. No. 12/539,153, filed Aug. 11, 2009, Tohyama, et al.
U.S. Appl. No. 12/936,282, filed Oct. 4, 2010, Ikarashi, et al.
Office Action issued Jun. 25, 2013 in Japanese Patent Application No. 2009-553318 with English language translation.
M. Zhu, et al., "Application of Radioligand-Receptor Binding Assays in the Search for the Active Principles of the Traditional Chinese Medicine 'Gouteng'", Phytotherapy Research, vol. 11, No. 3, 1997, pp. 231-236.

\* cited by examiner

*Primary Examiner* — Michael Pak
(74) *Attorney, Agent, or Firm* — Oblon, Spivak, McClelland, Maier & Neustadt, L.L.P.

(57) ABSTRACT

The invention intends to find out an in-vitro bioassay system capable of ensuring qualities of yokukansan to a higher degree, and provides a bioassay method for yokukansan, comprising competitively reacting labeled ligand and a test sample containing yokukansan with cells or cell membranes expressing serotonin 1A receptors, and measuring binding activity of yokukansan from the amount of the labeled ligand bound, and a bioassay method for yokukansan, comprising reacting labeled GTP and a test sample containing yokukansan with cells or cell membranes expressing serotonin 1A receptors, and measuring receptor-agonist activity of yokukansan from the amount of the labeled GTP bound.

9 Claims, 1 Drawing Sheet

BIOASSAY METHOD FOR YOKUKANSAN WITH SEROTONIN RECEPTOR

CROSS-REFERENCE TO RELATED APPLICATIONS

This application is a 371 of PCT/JP08/52550 filed Feb. 15, 2008.

TECHNICAL FIELD

The present invention relates to a method of bioassay of yokukansan, and more precisely, to an assay method capable of quantitatively determining the physiological activity level (pharmacological activity value) of yokukansan, a type of kampo preparation, by the use of action to serotonin (5-hydroxytryptamine) 1A (hereinafter referred to as "5HT1A) receptors.

BACKGROUND ART

A kampo preparation is a pharmaceutical prepared by blending crude drugs, in which all the active ingredients are not always specifically identified. Furthermore, a single active ingredient alone does not always exhibit its effect, and some active ingredients may compositely act with each other. For securing its quality, it is said that an assay method capable of totally evaluating the whole kampo preparation is necessary (Patent Document 1, Patent Document 2).

The assay method includes a method of total evaluation by assaying the individual ingredients, and a bioassay method of evaluating the physiological activity by the use of a biological material. The bioassay includes an in-vivo test and an in-vitro test, and the in-vivo test system has many limitations regarding the test facilities, test animals, the processing capability, and the like, and there were some difficulties in applying the in-vivo test to quality evaluation of kampo preparations.

On the other hand, the in-vitro test system does not require any special facilities and gives stable test results in a short period of time. For this reason, it is desired to establish a bioassay method with this system. In fact, for myostatin, a bioassay method is reported (Patent Document 3). However, for a kampo preparation that comprises a combination of crude drugs each having plural active ingredients by themselves, a suitable bioassay system could not always be found out, and the establishment of the bioassay system is desired.

For example, yokukansan, a type of kampo preparation, generally is a crude drug mixture having the composition shown below, or is its extract, and as necessary, further contains a pharmaceutical carrier such as an excipient and other ingredients usable on a pharmaceutical preparation. However, a suitable bioassay system is not yet found out for yokukansan. For securing higher quality for yokukansan, the development of the bioassay system for yokukansan is desired.

TABLE 1

| Ingredients | Amount |
| --- | --- |
| JP *Atractylodes Lancea* Rhizome | 4.0 g |
| JP *Poria* Sclerotium | 4.0 g |
| JP *Cnidium* Rhizome | 3.0 g |
| JP Japanese *Angelica* Root | 3.0 g |
| JP *Bupleurum* Root | 2.0 g |
| JP *Glycyrrhiza* | 1.5 g |
| JP *Uncaria* Hook | 3.0 g |

Patent Document 1: JP-T 2000-512621
Patent Document 2: JP-T 2001-521876
Patent Document 3: JP-T 2005-520486

DISCLOSURE OF THE INVENTION

Problems that the Invention is to Solve

Accordingly, the object of the present invention is to find out a bioassay system with an in-vitro test for yokukansan that secures higher quality of the kampo preparation.

Means for Solving the Problems

The present inventors have intensively studied on the effect of yokukansan, and as a result, they have found that the kampo preparation has binding activity to 5HT1A receptors, and its binding activity depends on the amount of yokukansan. Furthermore, the inventors have found that application of this finding may construct a bioassay method for yokukasan, and thus the present invention has been completed.

Specifically, the invention provides a bioassay method for yokukansan, comprising competitively reacting labeled ligand and yokukansan with cells or cell membranes expressing 5HT1A receptors, and measuring binding activity of yokukansan from the amount of the labeled ligand bound.

The invention further provides a bioassay method for yokukansan, comprising reacting labeled GTP and yokukansan with cell membranes expressing 5HT1A receptors, and measuring yokukansan from the amount of the labeled GTP bound.

Furthermore, the inventors have studied that Uncaria Hook, one of constituent crude drugs of yokukansan, has binding activity to 5HT1A receptors, and its binding activity depends on the amount of Uncaria Hook. The inventors have found that application of this finding may construct a bioassay method for Uncaria Hook or a test sample containing Uncaria Hook, and thus the present invention has been completed.

Examples of the test sample containing Uncaria Hook include kampo formulae such as shichimotsukokato, chotosan, yokukansan and yokukansan kachimpihange, each containing Uncaria Hook, and plant extract preparations containing Uncaria Hook.

Effects of the Invention

According to the bioassay method of the present invention, the physiological activity level (pharmacological activity value) of yokukansan, Uncaria Hook or a test sample containing Uncaria Hook can be determined stably and in a simplified manner by using an in-vitro test without limitation on the test facilities, test animals, the processing capability, and the like.

BEST MODE FOR CARRYING OUT THE INVENTION

The bioassay method for yokukansan of the present invention comprises using cells or cell membranes expressing 5HT1A receptors, measuring binding activity of yokukansan to the receptors, and determining the pharmacological activity value of yokukansan.

More specifically, any one of a method comprising competitively reacting labeled ligand and yokukansan with cells or cell membranes expressing 5HT1A receptors, and measuring binding activity of yokukansan from the amount of the labeled ligand bound (hereinafter referred to as a "first embodiment invention") and a method comprising reacting labeled GTP and yokukansan with cell membranes expressing 5HT1A receptors, and measuring agonist activity by receptor binding of yokukansan from the amount of the labeled GTP bound (hereinafter referred to as a "second embodiment invention") can be utilized.

Of the above two embodiment inventions, the first embodiment invention comprises competitively reacting labeled ligand and yokukansan with 5HT1A receptors expressed in cells or cell membranes, and measuring binding activity value of yokukansan from difference between a specific binding amount of the labeled ligand only and a binding amount of the labeled ligand after competition.

The cells expressing 5HT1A receptors used in the method of the invention include cells having human recombinant 5HT1A receptor expressing genes incorporated therein by the means of Newman-Tancredi, et al. (Newman-Tancredi, A. et al., 1992, High-level stable expression of recombinant 5-HT1A 5-hydroxytryptamine receptors in Chinese hamster ovary cells, Biochem. J. 285, 933-938). The examples include CHO cells, HeLa cells and the like expressing 5HT1A receptors. The cell membranes expressing 5HT1A receptors include cell membranes obtained by destroying the cells expressing 5HT1A receoptors by the means such as homogenate, and separating cell membrane fractions by the means such as high-speed centrifugal separation. Alternatively, commercially available 5HT1A receptor expressing cell membrane fractions may be used.

The labeled ligands to 5HT1A receptor include ligands labeled by radioisotope, fluorescence, enzymes and the like, and the examples thereof include [$^3$H]-8-OH-DPAT and [$^3$H]-5HT.

Specifically, the first embodiment invention is preferably carried out by using CHO cell membranes expressing 5HT1A receptors and determining binding activity from competition reaction between [$^3$H]-8-OH-DPAT and yokukansan. The reaction system in this case is preferably at about 25 to 37° C. The binding activity of the yokukansan is measured such that the labeled ligand and yokukansan are added to the cells or the cell membranes, and a reaction is conducted for about 15 to 60 minutes. Furthermore, the binding activity of yokukansan is preferably determined from difference between a specific binding amount of the labeled ligand only and a binding amount of the ligand after the competition reaction.

On the other hand, the second embodiment invention is based on the property that agonists bound to 5HT1A receptors expressed in cell membranes promote GDP-dissociation from G protein α subunit (hereinafter referred to as "Gα" for simplicity) of cell membranes and GTP subsequently replaces GDP on Gα subunit. In this case, agonist activity by 5HT1A receptor binding of yokukansan is determined from the amount of labeled GTP captured by Gα when yokukansan having agonist action was bound to the receptors.

The labeled GTP used in the second embodiment invention includes GTP labeled by radioisotope, fluorescence, enzymes and the like, and the examples thereof include [$^{35}$S]GTPγS and Europium-GTP.

To conduct the second embodiment invention, specifically, it is preferred to use CHO cell membranes expressing 5HT1A receptors, and to measure the binding amount of [$^{35}$S]GTPγS increased by agonist activity signal due to receptor binding of yokukansan. The second embodiment invention requires that the labeled GTP binds to Gα existing inside the cell membranes, and therefore, it is necessary to use cell membranes expressing 5HT1A receptors. In the case of utilizing cells expressing 5HT1A receptors, the labeled GTP cannot enter the cells, and yokukansan cannot be measured. Furthermore, the reaction of the second embodiment invention is preferably conducted at a temperature of about 22 to 30° C., and the reaction time is about 20 to 60 minutes. The receptor-agonist activity of yokukansan is preferably determined from a relative value between the labeled GTP binding amount of yokukansan and the labeled GTP binding amount by 5TH.

In the above both methods, it is generally preferred that a plural samples, preferably at least three samples each containing a known concentration of yokukansan are simultaneously measured, and the pharmacological activity (binding activity or receptor-agonist activity) value of yokukansan in these test samples is determined. However, so far as the condition does not almost differ, a calibration curve previously prepared from samples each containing a known concentration of yokukansan may be used for the determination.

As described above, the pharmacological activity value of yokukansan in test samples can be evaluated, and this action mechanism is considered as follows. Yokukansan and Uncaria Hook bind to 5HT1A receptors, and in the first embodiment invention, the labeled ligand bound to 5HT1A receptors is decreased according to the amount of the above ingredient as the result of competition reaction of the ingredient and the labeled 5HT1A ligand. Binding activity of yokukansan or Uncaria Hook can be determined by measuring the amount of the labeled ligand decreased in this way. The second embodiment invention utilizes the property of replacing GDP bound to Gα of cell membranes by GTP subsequent to binding of agonists to 5HT1A receptors. Specifically, yokukansan is reacted with 5HT1A receptors, and receptor-agonist activity of yokukansan is measured and evaluated from the amount of labeled GTP bonded to cell membrane Gα.

According to the bioassay method of the present invention described above, a standard preparation clinically recognized to have a pharmacological effect as yokukansan and a test preparation are evaluated for the pharmacological activity value under the same condition, and the standard preparation and the test preparation are compared with each other, thereby the quality equivalence of the preparation can be evaluated.

Also, when Uncaria Hook or a test sample containing Uncaria Hook is used in the bioassay method described above, the quality equivalence can be evaluated as it is for yokukansan.

Additionally, plural lots of preparations are evaluated for the pharmacological activity value according to the bioassay method of the present invention, and based on the uppermost and lowermost ranges derived from the mean data, the pharmacological activity value of the test samples can be evaluated as to whether or not it falls within the ranges, thereby the quality equivalence of the test preparations can be evaluated.

EXAMPLES

The present invention is described in more detail with reference to the following Examples. However, the invention should not be whatsoever restricted at all by these Examples.

Example 1

Serotonin 1A Receptor-Binding Inhibition Test
(Test Condition)
Cell membrane used: CHO cell membrane (expressing human recombinant 5HT1A receptor) (PerkinElmer)
Cultivation buffer solution: 50 mM Tris-HCl (pH 7.4) containing 0.1% ascorbic acid, 0.5 mM EDTA and 10 mM MgSO$_4$ Cultivation time and temperature: 60 minutes, 25° C.
Ligand: 1.5 nM [$^3$H]8-OH-DPAT(NET-929, 170.2 Ci/mmol, PerkinElmer)
Nonspecific ligand: 10 μM metergoline (Sigma)
Kd: 2 nM
Bmax: 1.3 pmol/mg protein
Specific binding: 75%

(Preparation of Test Drug Solution)

About 20 mg of a test drug (TJ-54 or extract of the constituent crude drug) was weighed. 100 μL (125 μL, for TJ-54) of distilled water was added to the test drug, and the same amount of DMSO was further added thereto, thereby preparing a 50% DMSO solution. The test drug solution was diluted to have each concentration.

(Binding Test of Test Drug)

32-46 μg protein/500 μL CHO cell membrane solution, 20 μL [$^3$H]8-OH-DPAT (final concentration: 1.5 nM) and 5.25 μL a test drug solution of each concentration (in vehicle, final concentration 0.5% DMSO) were added to a 1 mL tube, followed by incubation (60 minutes, 25° C.). After completion of the incubation, the resulting solution was filtered with a glass fiber filter (Whatman 1821-915 GF/B, Whatman) using a cell harvester (UNIFILTER-96, PerkinElmer). After washing the resulting solution 4 times with 50 mM tris-buffer solution, radioactivity of [$^3$H]8-OH-DPAT of the glass fiber filter was measured with a liquid scintillation counter (Top Count NXT, PerkinElmer). The nonspecific binding was calculated from radioactivity of [$^3$H]8-OH-DPAT in the presence of ligand unlabeled 10 μM metergoline, and the total binding was calculated from radioactivity of [$^3$H]8-OH-DPAT in the absence of a test drug (vehicle).

(Binding activity of a test drug was calculated using the following binding inhibition rate (%))

$$\text{Inhibition rate (\%)} = [1-(c-a)/(b-a)] \times 100$$

a: Average cpm of nonspecific binding
b: Average cpm of total binding
c: cpm in the presence of test compound (Result)

FIG. 1 shows the binding activity (%) of 200 μg/mL of yokukansan (TJ-54; Tsumura & Co.) and 7 extracts (50 μg/mL) of each constituent crude drug obtained by the above-described method. In these results, yokukansan and Uncaria Hook showed high binding activity. Furthermore, as shown in FIG. 2, dose dependency was recognized in those extracts.

The above results show that there is high correlation between the amount of yokukansan and the binding activity, and of the constituent crude drugs of yokukansan, there is high correlation between the amount of Uncaria Hook and the binding activity. The results mean that the pharmacological activity value of yokukansan can be measured by the method of Example 1, and the 5HT1A receptor-binding activity is induced by Uncaria Hook in yokukansan.

Example 2

$^{35}$S GTPγS (Serotonin 1A Receptor) Binding Test (Test Condition)

Cell membrane used: CHO cell membrane (expressing human recombinant 5HT1A receptor) (PerkinElmer)
Cultivation buffer solution: 100 mM NaCl, 10 mM MgCl$_2$, 1 mM DTT, and 20 mM HEPES (pH 7.4) containing 1 mM EDTA
Cultivation time and temperature: 30 minutes, 30° C.
Nonspecific ligand: 100 μM [$^{35}$S]GTPγS (SJ-1308, 1033 Ci/mmol, Amersham)

(Preparation of Test Drug Solution)

About 20 mg of a test drug (TJ-54 or extract of the constituent crude drug) was weighed. 100 μL (125 μL for TJ-54) of distilled water was added to the test drug, and the same amount of DMSO was further added thereto, thereby preparing a 50% DMSO solution. The test drug solution was diluted to have each concentration.

([$^{35}$S]GTPγS Binding Test)

50 μL of CHO cell membrane solution (25-30 μg protein/mL), 0.42 μL of a test drug solution of each concentration (in vehicle, final concentration 0.4% DMSO), and 25 μl of a GDP (10 μM) solution were incubated on a 96-well plate in HEPES (pH 7.4) buffer solution (20 minutes, 30° C.). 25 μL of SPA beads (Scintillation Proximity Assay beads; GE Amersham) was then added, followed by further incubation (60 minutes, 30° C.). Thereafter, for the measurement of radioactivity, 10 μL of [$^{35}$S]GTPγS (0.3 nM) was added, followed by incubation (30 minutes, 30° C.).

After completion of the incubation, radioactivity was measured with a liquid scintillation counter (MicroBeta, PerkinElmer). [$^{35}$S]GTPγS binding rate (%) of the test drug was calculated by the following equation, and used as agonist activity. Nonspecific binding was calculated from activity between ligand unlabeled 100 μM GTPγS and [$^3$H]8-OH-DPAT.

(Calculation of [$^{35}$S]GTPγs Binding Rate of Test Drug)

$$\text{Binding rate (\%)} = [(c-a)/(b-a)] \times 100$$

a: Average cpm of nonspecific binding
b: Average cpm in the presence of 300 nM serotonin
c: cpm in the presence of test compound (Results)

Using yokukansan (TJ-54, Tsumura & Co), agonist activity (%) at each concentration was obtained by the above method. Regarding seven crude drugs constituting yokukansan, the agonist activity (%) was similarly obtained. Of those results, agonist activities about yokukansan and Uncaria Hook are shown in FIG. 3.

These results show that there is high correlation between the amount of yokukansan in a range of 12.5 to 200 μg/mL and the agonist activity, and there is also high correlation between the amount of Uncaria Hook and the agonist activity.

INDUSTRIAL APPLICABILITY

According to the present invention, the pharmacological activity value of yokukansan can be determined stably and in a simplified manner by using an in-vitro test without limitations on the test facilities, test animals, the processing capability, and the like.

Accordingly, as compared with the conventional method in which a predetermined constituent is subjected to analysis, the invention makes it possible to secure the quality of yokukansan to a higher degree.

Figure 1:
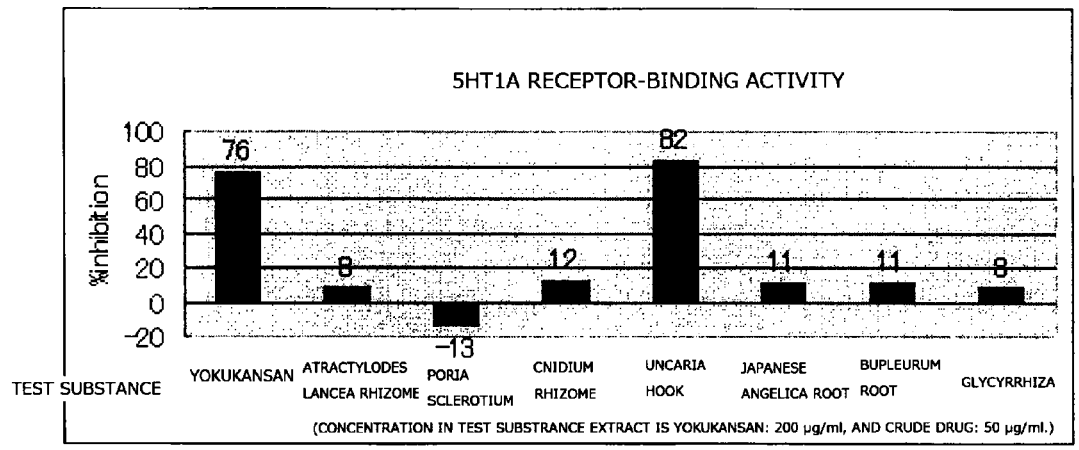
FIG. 1 is a view showing 5HT1A receptor-binding activity of yokukansan and 5HT1A receptor-binding activities of seven crude drugs constituting yokukansan.
Figure 2:
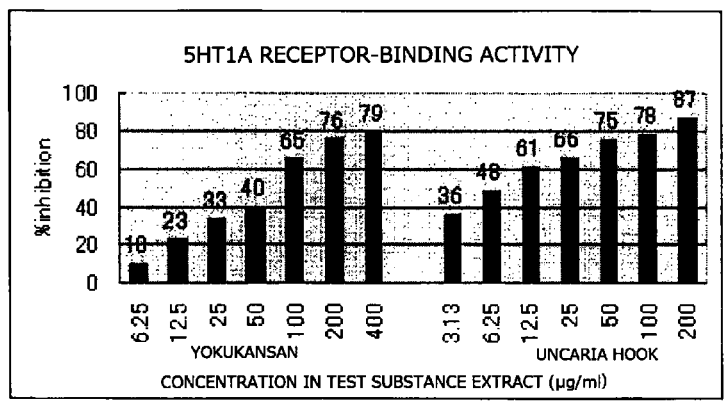
FIG. 2 is a view showing 5HT1A receptor-binding activity of yokukansan and 5HT1A receptor-binding activity of Uncaria Hook, at each concentration.
Figure 3:
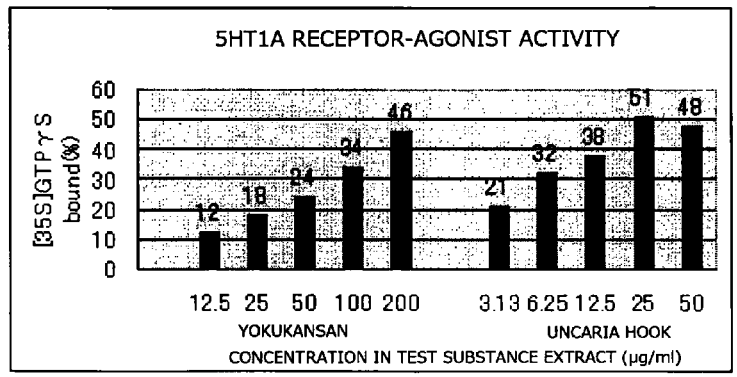
FIG. 3 is a view showing [$^{35}$S]GTPγS-binding activity of yokukansan and [$^{35}$S]GTPγS-binding activity of Uncaria Hook, at each concentration.

The invention claimed is:

1. A bioassay method for yokukansan, comprising competitively reacting labeled ligand and yokukansan with cells or cell membranes expressing a serotonin 1A receptor, and measuring serotonin 1A receptor-binding activity of yokukansan from the amount of the labeled ligand bound wherein the labeled ligand specifically binds serotonin 1A receptor.

2. A bioassay method for yokukansan, comprising competitively reacting labeled GTP and yokukansan with cell membranes expressing a serotonin 1A receptor, and measuring agonist activity by serotonin 1A receptor binding of yokukansan from the amount of the labeled GTP bound by G protein $\alpha$ when yokukansan having agonist action was bound to the receptor.

3. The bioassay method of claim 1, comprising competitively reacting the labeled ligand and yokukansan with cells, wherein the cells are Chinese hamster ovary cells or HeLa cells expressing a serotonin 1A receptor.

4. The bioassay method of claim 1, comprising competitively reacting the labeled ligand and yokukansan with cell membranes, wherein the cell membranes are obtained by homogenating cells expressing a serotonin 1A receptor and separating a cell membrane fraction by centrifugation.

5. The bioassay method of claim 2, comprising competitively reacting the labeled GTP and yokukansan with cell membranes, wherein the cell membranes are obtained by homogenating cells expressing a serotonin 1A receptor and separating a cell membrane fraction by centrifugation.

6. The bioassay method of claim 1, further comprising correlating the serotonin 1A binding activity with yokukansan quality.

7. The bioassay method of claim 6, wherein the correlating comprises comparing the serotonin 1A binding activity with a set of data.

8. The bioassay method of claim 1, further comprising correlating serotonin 1A binding activity with pharmacological activity of yokukansan in a kampo preparation.

9. The bioassay method of claim 2, further comprising correlating agonist activity by serotonin 1A with pharmacological activity of yokukansan in a kampo preparation.

* * * * *